United States Patent [19]

Dorr

[11] 4,184,593
[45] Jan. 22, 1980

[54] PACKAGE FOR DISPOSABLE SYRINGES

[76] Inventor: Paul E. Dörr, Wunderlichstr. 3, D-8000 Munich 70, Fed. Rep. of Germany

[21] Appl. No.: 809,413

[22] Filed: Jun. 23, 1977

[30] Foreign Application Priority Data

Jul. 1, 1976 [DE] Fed. Rep. of Germany ........ 2629557

[51] Int. Cl.² .................. B65D 79/00; A61M 5/18
[52] U.S. Cl. .................. 206/365; 128/218 R; 128/215
[58] Field of Search .......... 206/365; 128/215, 218 R, 128/218 D, DIG. 5, 272, 220

[56] References Cited

U.S. PATENT DOCUMENTS

| 2,372,469 | 3/1945 | Beasley et al. | 128/220 |
| 2,720,969 | 10/1955 | Kendall | 206/365 |
| 3,316,909 | 5/1967 | Cowley | 128/218 R |
| 3,545,607 | 12/1970 | Keller | 206/365 |
| 3,642,123 | 2/1972 | Knox | 206/365 |
| 3,746,155 | 7/1973 | Seeley | 206/365 |
| 3,826,261 | 7/1974 | Killinger | 128/272 |
| 3,869,062 | 4/1975 | Jaeschke et al. | 206/365 X |
| 3,921,633 | 11/1975 | Tischlinger | 128/215 X |
| 3,978,858 | 9/1976 | Tischlinger | 128/218 P X |

FOREIGN PATENT DOCUMENTS 2131202 11/1972 Fed. Rep. of Germany .......... 206/365

Primary Examiner—Davis T. Moorhead
Attorney, Agent, or Firm—Cushman, Darby & Cushman

[57] ABSTRACT

A disposable syringe divided into two units to be packed separately under sterile conditions. The first unit contains a filled cylindrical ampoule with a plug serving as piston and a pierceable seal. The other unit contains a needle, a needle cover which serves as piston rod and a holder for the needle and the ampoule. The second unit contains also a finger rest having a sleeve slidable along the ampoule to a stop on its rear end.

16 Claims, 11 Drawing Figures

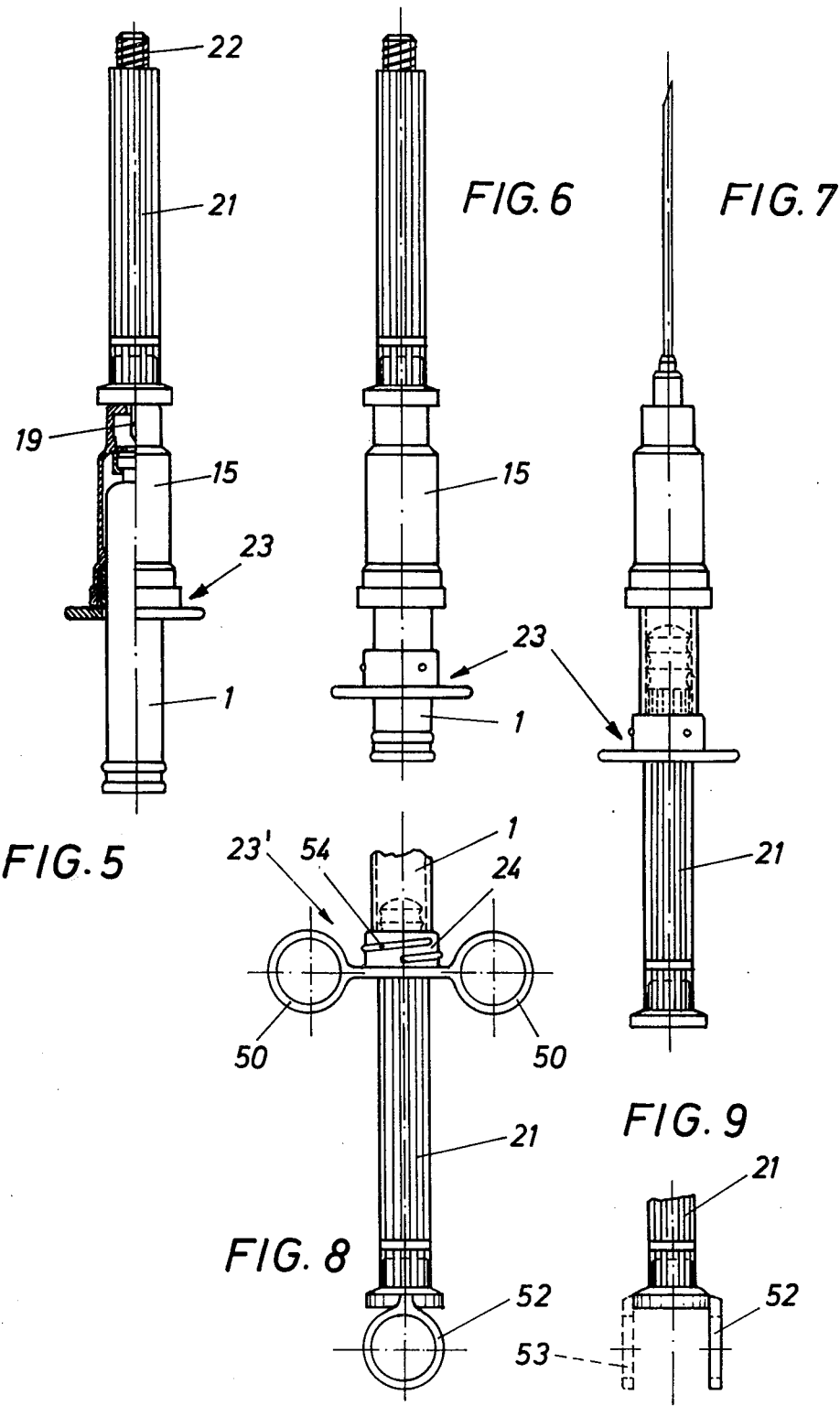

PACKAGE FOR DISPOSABLE SYRINGES

The invention relates to disposable syringes suitable for injecting a liquid subcutaneously or intra-arterially into a human or animal body.

Disposable syringes of this general kind are known from my German patent specification No. 2,131,202. As stated in that specification, work carried out in a sterile area is expensive. A two-part syringe reduces the amount of work which has to be performed in a sterile area, as the part comprising the needle, needle cover and holder may be packed outside and subsequently sterilised. Only the part comprising the ampoule has to be filled in a sterile area. It would be difficult, if not impossible, for sterilisation to be carried out afterwards. Contrary to the statement in the patent specification, the cylindrical ampoules are not equipped with a cap acting as sterile cover for the seal, as, according to recently acquired knowledge, protection is to be extended to the rear end opening of the cylindrical ampoule. Rather the cylindrical ampoules are packed, under sterile conditions, into films in the sterile room thus using less space and permitting the work to be carried out at less cost, less interference and increased safety in the sterile area.

There are few applications for which syringes, including those with cylindrical ampoules, require a finger rest; these are, in particular, intra-articular and subcutaneous injections. For other applications, however, such as intravenous an intramuscular injections, there is no need for the finger rest, because the cylindrical ampoule is handled conveniently by the doctor on its cylindrical part only.

It would be impracticable if the cylindrical ampoules would have to be manufactured partly with and partly without the finger rest. This would have the effect of doubling the number of different sizes of cylindrical ampoules, which would mean smaller batches and storing double the amount, or in other words, higher costs. What is more important, however, is that a cylindrical shape without finger rest is required for processing and packing cylindrical ampoules in the sterile room, as this would very largely simplify the handling by machine. Thus the requirement is to provide for a finger rest to be attached on the cylindrical ampoule if the need arises.

The requirement of this invention is to develop the disposable syringe of the kind mentioned in such a way that the cylindrical ampoules to be packed in the sterile room are without finger rest, but that the user has a finger rest at his disposal if he needs one. A further requirement is to vary the syringes for the different applications in such a way that finger rests are included in some packs but not in others where they are not needed.

The invention provides a disposable syringe comprising two parts: a first part comprising a filled cylindrical ampoule, a plug closing a rear end of the ampoule and serving as a piston for driving out the filling from the ampoule, a stop projecting laterally from the rear end of the ampoule, and a piercable seal closing a front end of the ampoule; a second part comprising a holder for the ampoule and for a needle whereby a length of needle can be held for piercing the seal closing the front end of the ampoule, the holder being shorter than the ampoule, and a hollow needle cover shaped as a piston rod for connecting to the plug; and a separate finger rest having a sleeve slidable along the ampoule to the stop.

Only the cylindrical ampoules need be packed in a sterile area. A finger rest is available if needed. The finger rest is separate from the ampoule and packed with the other components of the syringe.

After removing the wrappings, the user pushes the front end of the cylindrical ampoule through the finger rest. He then fits it into the holder and pierces the seal. The finger rest is pulled to the rear end of the ampoule, where the end stop prevents it from sliding off. This is done without additional effort by placing the thumb on the rear opening of the cylindrical ampoule and pulling the finger rest into its desired final position using forefinger and middle finger. The needle cover is then used as a piston rod for the syringe.

The finger rest may be packed loosely on its own, but the assembly of the syringe by the user is made easier by making the sleeve of the finger rest receivable in the ampoule holder. The end of the holder may be appropriately widened and fitted with the finger rest. The inside of the end of the holder may be provided with a circumferential ridge for engaging with projections on the sleeve of the finger rest. Alternatively, the holder may similarly be provided with a groove.

The ampoule holder and finger rest may be made of different materials, matched to ensure smooth sliding, locking and unlocking.

The finger rest is preferably generally rectangular, but with rounded corners, to facilitate packing by machine. The finger rest can thus readily be joined to the holder by machine and positioned with accuracy. If the finger rest has to be shifted during packing, it does not wobble.

The syringe may be equipped with rings on the outside of the sleeve or holder and the end of the needle cover for the fingers and thumb of a user to facilitate single-handed use of the syringe when aspirating, i.e. drawing fluid in from the body to find out if a blood vessel has been hit. The space required for packing the finger rest and/or needle holder is not critical. The two rings on the finger rest or holder are for the fore and middle fingers, whilst that or those at the end of the needle cover are for the thumb.

The cylindrical ampoule, being separate from the finger rest can be packed by machine into a small sterile film. Apart from protruding sealed-off rims, the pack may have a diameter which differs from that of the ampoule by little more than the thickness of the film. Thus the packs may be pushed into an oblong recess in a blister pack having also a recess or recesses for other parts of the syringe. The film may be specially drawn on one side to produce the recess for the ampoule. This drawn-out part may also serve for receiving a needle if the holder itself has no complete needle. Such holders have only the length of needle for piercing the ampoule and a cone for fitting a separate needle. The recesses in one side of the pack may between them provide a recess in the other side of the pack, and the recesses may be formed so as to lock a syringe part in that on the other side of the pack. The pack may comprise a three-rim-sealed bag or envelope, and the sealed or welded pack may be provided with a pull-open device.

Packing is generally carried out immediately after filling the ampoule and checking of the filling level. The ampoules are then removed from the sterile area. Suspensions which, for safety reasons, have to be inspected by hand for foreign bodies, may be inspected at less cost under non-sterile conditions by looking through the film. Printing or stamping, possibly in mirror writing on the inside of the film at about the level of the plug, permits localisation of the cylindrical ampoule. Normally this is not possible because of the siliconising of the ampoule which prevents print or labels from sticking to it. Stamping of the ampoule cap, which is known to be difficult, can thus be avoided.

The invention is illustrated by way of example in the drawings of which:

FIGS. 5 to 7 show three stages of putting the disposable syringe into use;

FIG. 8 shows a modified disposable syringe suitable for aspirating;

FIG. 9 shows a detail perpendicular to FIG. 8;

Figure 2:
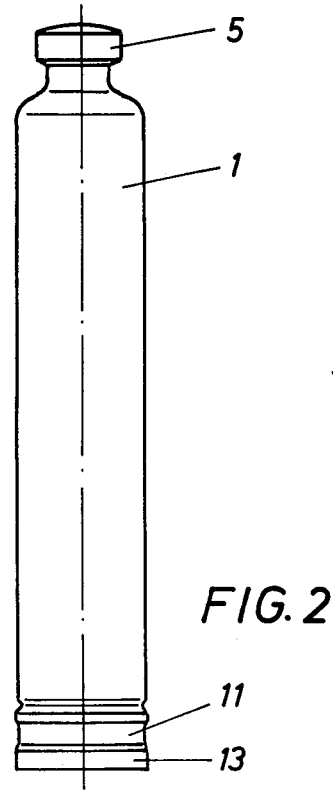
FIG. 2 shows a cylindrical ampoule of the syringe.
Figure 4:
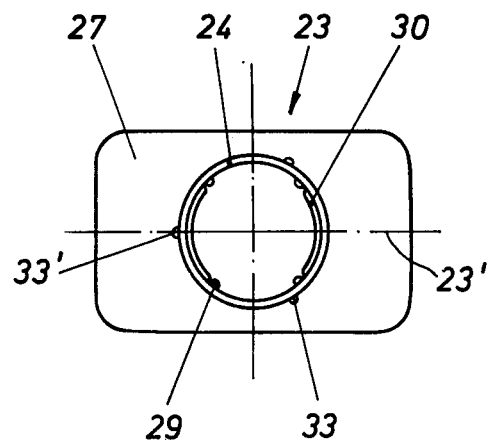
FIG. 4 shows a plan of the finger rest of FIG. 3.
Figure 11:
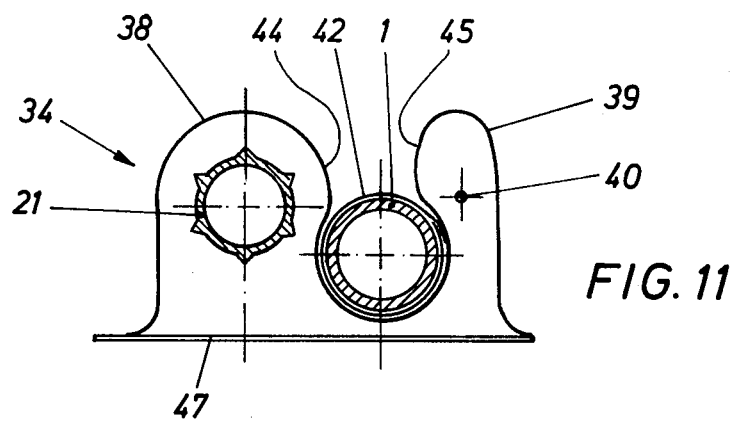
FIG. 11 is a section along line XI—XI in FIG. 10.
Figure 10:
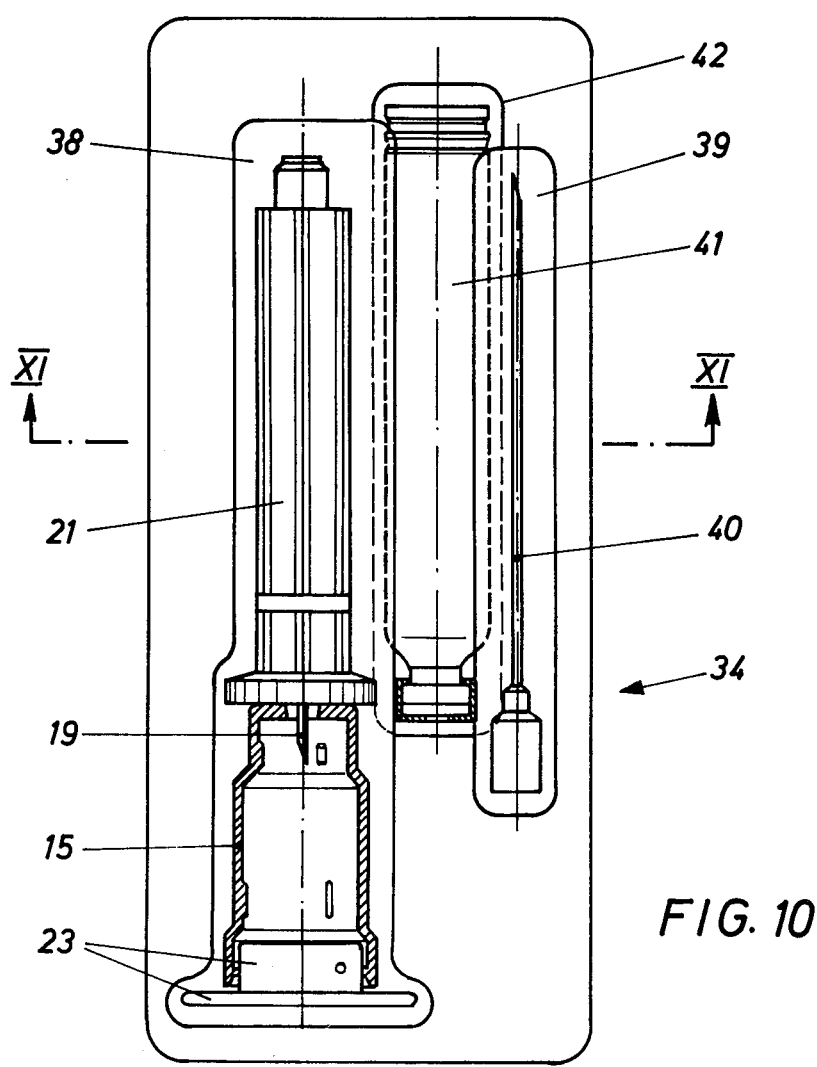
FIG. 10 shows a plan of a blister pack containing the disposable syringe of FIGS. 1 to 4.

With particular reference to FIG. 2, a filled cylindrical ampoule 1, at the front end, has a seal to be pierced which is supported by a flanged aluminium cap 5 with a central opening. In the lower end is a plug with an internal thread to serve as a piston for driving out the filling. Just above the lower end of the ampoule 1, there is an annular groove 11. Thus a collar 13 is produced at the very bottom which has the same diameter as the ampoule 1 itself. In this way, there is created an end stop projecting laterally for the finger rest.

Figure 1:
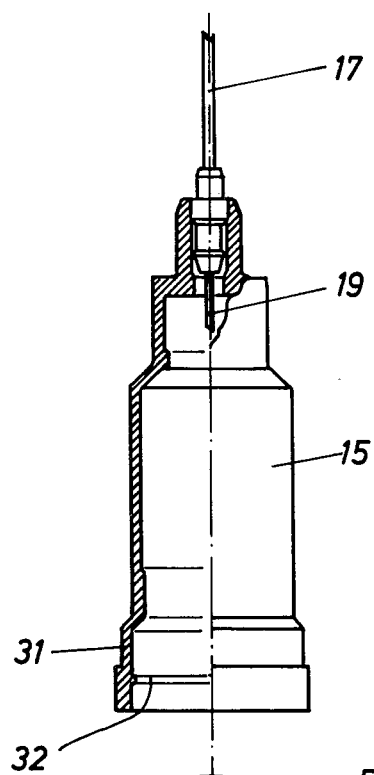
FIG. 1 shows a holder of a disposable syringe with a needle with broken-off top.

In FIG. 1, a holder 15 for the ampoule 1 carries a needle 17 having a length 19 protruding inwards for piercing the seal. A needle cover 21 (FIGS. 5 to 7) with a threaded nipple 22 can be used as a piston rod for the plug.

Figure 3:
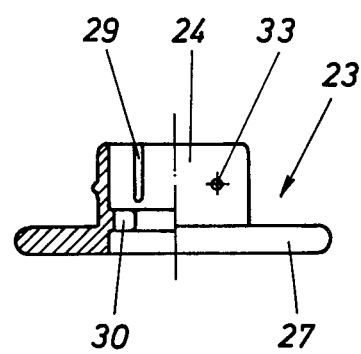
FIG. 3 shows a finger rest of the syringe.

The finger rest 23 of FIG. 3 comprises a sleeve 24 and a finger rest plate 27 attached in a flange-like manner to the sleeve 24. The plate 27 is of rectangular shape and has rounded-off corners. The sleeve 24 has four ribs 29 on the inside extending parallel to the axis of the sleeve, and two annular ridges 30 each subtending an angle of approximately 90° along the circumference. The dimensions of the sleeve 24 are such that by deforming it, it can just be pushed over the ampoule 1. The annular ridges 30 slot into the annular groove 11 at the lower end of the ampoule 1 where they retain the finger rest 23 ready for use.

At the bottom, the holder 15 has an enlarged section 31 with an annular inner ridge 32. On the outside of the sleeve 24, there are small approximately-conical projections 33 equally spaced around the circumference. When the sleeve 24 is pushed into the enlarged section 31, the projections 33 fit the inner ridge 32 and secure the finger rest 23 to the holder 15 for transport and packing. One of the projections (33'), is on a longitudinal centre plane 23' of the finger rest 23.

The ampoule 1 is wrapped on its own in a film which is sealed and/or welded around it. All other parts are packed together outside the sterile area, sterilised and placed into a blister or peel pack 34. The pack 34 has deep-drawn parts 38 and 39 which are shaped to match the items to be packed. The deep-drawn part 38 receives the holder 15 with needle, needle cover 21 and finger rest 23. Further items such as an alcohol swab or a plaster may also be housed in this space. The deep-drawn part 39 may be empty or used for housing a needle 40 (if the holder 15 does not have a complete needle but only has a length of needle 19) and a mounting cone for a separate needle on the outside end.

The two deep-drawn parts 38 and 39 form an oblong recess 41 for receiving the ampoule 1 sealed on its own into a film 42 from the other side of the pack. The distance between the side walls 44, 45 of the deep-drawn parts 38 and 39 at the edge of the recess 41, is smaller than the diameter of the ampoule. The ampoule 1 pressed into the recess 41 is firmly retained in its place. After filling, the pack 34 is sealed with resistant paper 47 which is permeable to gas but not to bacteria. In this way gas sterilisation is possible.

FIGS. 5 to 7 show the operations for putting the syring into use. Initially the ampoule 1 is pushed from behind into the holder 15 which holds the finger rest 23, and is moved far enough forward to allow the length of needle 19 to pierce its seal. Then the thumb is placed on the rear end of the ampoule 1 and, using fore and middle finger, the finger rest 23 is pulled backward and released from the holder 15. The finger rest 23 ends up by locking into the lower end of the ampoule 1 (FIG. 6). Finally, the needle cover 21 is removed from the needle and used as a piston rod (FIG. 7).

To obtain a single-handed syringe for aspirating, rings 50 are provided (FIGS. 8 and 9) on the sleeve 24 of the finger rest 23' for inserting fore and middle finger, and a ring 52 for receiving the thumb is provided at the open end of the needle cover 21. The ring on the end of the needle cover 21 is fitted as shown in FIG. 9 so as not to obstruct the push-fit of the needle cover 21 onto the holder 15. A further similar ring 53 is provided opposite the ring 52 to facilitate control over the needle cover 21 serving as a piston rod during injection. FIG. 8 shows locking elements of a different kind for the finger rest, that is an outside thread 54 which may be screwed into an inside thread (not shown) of the holder 15. Prior to insertion into the blister pack, the ampoule 1 is sealed into a three-rim-sealed bag. Alternatively it may be wrapped up like a roll of coins. The longitudinal seam is sealed or welded along the entire length of the material needed, longer than the ampoule itself. Then two small end seams are welded. In order to overcome the tube-end effect, the ends may be shortened by turning them through 180°. The film pack for the cylindrical ampoule is stamped in mirror writing from inside. In this way it is not possible to forge the expiry date or other information without unpacking the ampoule and thus rendering it unusable. The deep-drawn parts 38 and/or 39 of the pack may be similarly marked. Imprinting or stamping of the film for the cylindrical ampoule is at the level of the piston of the ampoule, where it will not interfere with visual inspection for suspended particles.

What I claim is:

1. A packaged disposable syringe arrangement comprising:

a first part comprising a sterilized filled cylindrical ampoule including a plug closing a rear end of the ampoule and serving as a piston for driving out the filling from the ampoule, a finger rest stop on the rear end of the ampoule, a piercable seal closing a front end of the ampoule, and a removable sealed wrapping means around said ampoule for maintaining the ampoule sterilized;

a second part separate from said first part and comprising a needle, a holder for the ampoule and for said needle whereby a partial length of said needle is inwardly held for piercing the seal closing the front end of the ampoule, the remaining length of said needle extending exteriorly of said holder, said holder being shorter than the ampoule, and a hollow needle cover covering remaining needle length and being shaped as a piston rod for connecting to the plug;

a third part including a separate finger rest having a sleeve slidable along the ampoule toward said rear end to said stop; and packaging means for retaining said parts including retaining said wrapped first part separate from the other parts and having a gas permeable seal for permitting sterilization of said second and third parts to the exclusion of said sterilized wrapped first part.

2. A disposable syringe according to claim 1 in which the sleeve is receivable in the ampoule holder.

3. A disposable syringe according to claim 2 in which the sleeve or the holder is provided with lateral projections, and the other of these parts with an internal ridge or groove whereby the sleeve is retained in the holder.

4. A disposable syringe according to claim 1 in which the ampoule holder and finger rest are made of different materials, matched to ensure sliding, locking, and unlocking.

5. A disposable syringe according to claim 1 in which the finger rest is generally rectangular but with rounded corners.

6. A disposable syringe according to claim 1 which is equipped with rings on the outside of the sleeve or holder and the end of the needle cover for the fingers and thumb of a user to facilitate single-handed use when aspirating.

7. A disposable syringe according to claim 1 wherein said packaging means includes a blister pack and in which at least the said first and second parts are respectively in separate exterior and interior recesses of said blister pack, said exterior recess having an open mouth formed for a snap-in fit for said first part.

8. A packaged disposable syringe arrangement comprising:

a first part comprising a sterilized filled cylindrical ampoule including a plug closing a rear end of the ampoule and serving as a piston for driving out the filling from the ampoule, a finger rest stop at the rear end of the ampoule, a piercable seal closing a front end of the ampoule, and a removable sealed wrapping means around said ampoule for maintaining the ampoule sterilized;

a second part comprising a holder for the ampoule and for a needle whereby a length of needle can be held for piercing the seal closing the front end of the ampoule, the holder being shorter than the ampoule, and a hollow needle cover shaped as a piston rod for connecting to the plug;

a third part including a separate finger rest having a sleeve slidable along the ampoule toward said rear end to said stop; and packaging means for retaining said parts and having a gas permeable seal for permitting sterilization of said second and third parts wherein said packaging means includes a blister pack and in which at least the said first and second parts are in separate recesses of said blister pack, and in which two recesses in one side of said blister pack provide between them a recess in the other side of the pack.

9. A disposable syringe according to claim 8 in which the recesses are formed so as to lock a syringe part in that on the other side of the pack.

10. A disposable syringe according to claim 9 in which the ampoule is packed in a three-rim-sealed bag comprising said sealed wrapping means.

11. A disposable syringe according to claim 1 in which said sealed wrapping means closely surrounds said ampoule as a sterile packing comprised of a three-rim-sealed bag or an envelope, sealed off by welding or sealing, and equipped with a pull-open device.

12. A disposable syringe according to claim 1 in which said wrapping means is a sterile packing including a film or film combination and the film or film combination is imprinted or stamped in mirror writing on its inside at the level of the piston plug of the cylindrical ampoule.

13. A packaged disposable syringe arrangement comprising:

a first part comprising a sterilized filled cylindrical ampoule including a plug closing a rear end of the ampoule and serving as a piston for driving out the filling from the ampoule, a finger rest stop on the rear end of the ampoule, a piercable seal closing a front end of the ampoule, and a removable sealed wrapping means around said ampoule for maintaining the ampoule sterilized;

a second part comprising a holder for the ampoule and for a needle whereby a length of needle can be held for piercing the seal closing the front end of the ampoule, the holder being shorter than the ampoule, and a hollow needle cover shaped as a piston rod for connecting to the plug; and packaging means for retaining said parts separately and including means for permitting sterilization of said second part to the exclusion of said sterilized wrapped first part.

14. A disposable syringe as in claim 13 wherein said finger rest stop has a maximum lateral dimension substantially the same as said ampoule.

15. A disposable syringe as in claim 1 wherein said finger rest sleeve and ampoule holder have cooperative uniting means for holding the sleeve and holder together at the holder end opposite said needle.

16. A disposable syringe as in claim 1 wherein said ampoule and finger rest sleeve are so constructed that the sleeve can be put on the ampoule at its front end and slid over the ampoule to said rear end stop.

* * * * *